United States Patent [19]
Holtman et al.

[11] Patent Number: 5,704,931
[45] Date of Patent: Jan. 6, 1998

[54] ABSORBENT ARTICLE HAVING A DEFORMATION RESISTING APPARATUS

[75] Inventors: Dennis C. Holtman, Flemington, N.J.; Michael J. Menard, Doylestown, Pa.

[73] Assignee: McNeil-PPC, Inc., Skillman, N.J.

[21] Appl. No.: 100,598

[22] Filed: Jul. 30, 1993

Related U.S. Application Data

[63] Continuation of Ser. No. 753,515, Sep. 3, 1991, abandoned.

[51] Int. Cl.$^6$ .................................................. A61F 13/15
[52] U.S. Cl. ..................... 604/387; 604/385.1; 604/393; 604/397
[58] Field of Search ............................. 604/358, 385.1, 604/386, 390, 393, 397, 398, 400

[56] References Cited

U.S. PATENT DOCUMENTS

| | | | |
|---|---|---|---|
| 2,964,041 | 12/1960 | Ashton et al. | 128/290 |
| 3,262,451 | 7/1966 | Morse | 128/290 |
| 3,407,814 | 10/1968 | George et al. | 128/290 |
| 3,570,493 | 3/1971 | Olsson | 128/290 |
| 4,195,634 | 4/1980 | DiSalvo et al. | 128/290 |
| 4,217,901 | 8/1980 | Bradstreet et al. | 128/290 |
| 4,605,405 | 8/1986 | Lassen | 604/390 X |
| 4,609,373 | 9/1986 | Johnson | 604/390 X |
| 4,685,914 | 8/1987 | Holtman | 604/368 |
| 4,865,597 | 9/1989 | Mason, Jr. et al. | 604/386 |
| 5,087,254 | 2/1992 | Davis et al. | 604/385.1 X |
| 5,098,422 | 3/1992 | Davis | 604/385.1 |
| 5,197,959 | 3/1993 | Buell | 604/385.1 |
| 5,221,275 | 6/1993 | Van Iten | 604/387 |

FOREIGN PATENT DOCUMENTS

| | | |
|---|---|---|
| 0 298 348 | 1/1989 | European Pat. Off. . |
| 0 335 252 A2 | 10/1989 | European Pat. Off. . |
| 0 337 438 A1 | 10/1989 | European Pat. Off. . |
| 0 464 856 A2 | 1/1992 | European Pat. Off. . |
| 1307559 | 9/1962 | France . |
| 2161384 | 1/1986 | United Kingdom ........ 604/385.1 |

OTHER PUBLICATIONS

EP Search Report.

*Primary Examiner*—John G. Weiss
*Assistant Examiner*—Dennis Ruhl

[57] ABSTRACT

An absorbent article is provided having an apparatus attached to its garment facing side which allows the article to be attached to, and yet float on, an undergarment and which also serves to distribute the forces imposed on the article by the user's body over a large portion of the article and to transmit the forces to the undergarment, thereby increasing the geometric stability and shape maintenance of the article. The apparatus comprises a semi-rigid elastic frame formed from a thin plastic sheet and having two longitudinally extending members connected by at least one transversely extending member. Inwardly extending tabs for attaching the article to an undergarment are disposed at the mid-point of each longitudinally extending member. The longitudinally and transversely extending members may be pre-formed to give the article an arcuate shape. When applied to a winged article, the frame may also have outwardly extending tabs, disposed opposite each of the inwardly extending tabs, for properly positioning the wings.

25 Claims, 9 Drawing Sheets

ABSORBENT ARTICLE HAVING A DEFORMATION RESISTING APPARATUS

This is a continuation of application Ser. No. 07/753,515, filed Sep. 3, 1991 now abandoned.

FIELD OF THE INVENTION

The current invention concerns an absorbent article for use in the perineal area of the body. More specifically, the invention concerns an absorbent article which resists permanent deformation by use of a device for attaching the article to an undergarment which allows the article to float on the undergarment and which distributes and transmits forces imposed on the article, thereby providing the article with increased geometric stability and shape maintenance.

BACKGROUND OF THE INVENTION

Commonly used absorbent article, such as sanitary napkin, panty liners, and incontinency pads are generally worn in conjunction with an undergarment, such that the absorbent article is interposed between the user's body and the undergarment. The undergarment provides a means for holding the article against the user's body.

A variety of methods of attaching such absorbent articles to the undergarment are known in the art. Early designs were simply pinned in place. Subsequent developments resulted in the application of one or more strips of adhesive to the garment facing side of the article which anchored it in a fixed relation to the undergarment. More recently, it has been proposed that a high-friction material be applied to or made part of the garment facing side of the article. Again, the purpose of the high-friction material is to anchor the article to the undergarment in a fixed relation.

Unfortunately, anchoring to the undergarment by adhesives or other means does not present an optimal solution to the problem of attaching the absorbent product to the body. As the user goes about his or her activities, the position of the garment relative to the body shifts. Consequently, friction between the body and the absorbent article acts to deform the absorbent product. These forces have three sets of components. They are (i) lateral forces which tend to compress the product, (ii) tensile forces which tend to stretch the absorbent product, and (iii) shearing forces which act to deform the product either in the plane of the crotch of the undergarment or out of the plane of the crotch of the undergarment.

The stretching can cause a "necking down" of the product as well as curling. In addition, stretching can weaken and break the internal absorbent pad. The compression from the sides can cause a reduction in the area of the absorbent product. This reduces the target area for fluids. Compression on the sides also can cause curling of the product. Combined with the shearing forces, the net effect of these forces is that the absorbent article shifts, deforms, and becomes a product which is crushed transversely inwardly and its edges are curled around its longitudinal axis so that the napkin eventually takes on the appearance of a twisted rope. Hence, the phenomenon is known as "roping". Besides being uncomfortable to the user, the resulting product has a smaller strike zone to catch body exudate and thus is less effective in intercepting body fluids. This results in more frequent leakage of the product.

Even in the dry state, the reaction of the absorbent body to the forces imposed on it is a combination of elastic and inelastic responses. To small deforming pressures, the absorbent body yields. When the force is removed, the absorbent body tends to return to its original position. This is essentially an elastic response. When the force is greater and exceeds the elastic limit of the absorbent body, the product yields under pressure but does not return completely when the pressure is removed. This is an inelastic response.

If the absorbent structure is comminuted pulp, as in current diapers and external sanitary protection products, in the wet state the absorbent product has even less ability to provide an elastic response than it does in the dry state. Due to plasticization by water, the wet inelastic response is increased and the wet elastic response is decreased.

One means of improving the absorbent product would be to enhance its elastic response in both the dry and the wet state. This can be done by adding a reinforcing member to an absorbent article, such as proposed by U.S. Pat. No. 4,865,597 (Mason et al.); U.S. Pat. No. 3,570,493 (Olsson), U.S. Pat. No. 4,195,634 (DiSalvo et al.) and U.S. Pat. No. 3,407,814 (George et al.). The difficulty with this approach is that when the stiffness has been increased to the degree necessary to be effective in an article maintained in a fixed relation to the undergarment by adhesive, it is likely that the user will find the pressure against the thighs uncomfortable.

A more desirable alternative to coping with the deforming forces is to absorb the forces in a harmless way which will not result in permanent deformation of the absorbent article. Ideally, the energy from the environment should be transferred or dissipated with a minimum effect on the absorbent body itself.

Consequently, it would be desirable to provide an apparatus that attached the absorbent article to an undergarment in such a way that the article floated thereon while maintaining flexibility for comfort and resiliency for durability as well as dimensional stability.

Although attachment of the article to the undergarment via positioning and retaining straps so as to allow the article to move relative to the undergarment has been suggested, see U.S. Pat. No. 4,605,405 (Lassen), such straps are cumbersome and do not provide sufficient geometric stability to allow adequate relative motion to prevent permanent deformation.

Consequently, it would be desirable to provide an apparatus that attached the absorbent article to an undergarment in such a way that the article floated thereon while maintaining flexibility for comfort and resiliency for durability as well as dimensional stability.

Moreover, although it is known to pre-form an absorbent article into an arcuate shape in the longitudinal direction such that the body facing side has a longitudinally concave shape—for example, see U.S. Pat. No. 3,262,451 (Morse) and U.S. Pat. No. 2,964,041 (Ashton et al.)—the inventor has discovered that improved performance can be obtained by pre-forming the article into an arcuate shape in the transverse direction such that the body facing said has a transversely convex shape. Consequently, it would be desirable to provide an apparatus which readily allowed pre-forming the article into such an arcuate shape.

SUMMARY OF THE INVENTION

It is an object of the current invention to provide an absorbent article having an apparatus attached thereto which provides the article with a mechanism for resisting permanent deformation by (i) attaching the article to an undergarment so as to allow the article to float thereon in response to the forces imposed on it by the user's body, (ii) distributing the forces imposed on the article throughout a large portion of the article, and (iii) transmitting theses forces to the elastic in the panty crotch.

It is another object of the invention that the apparatus be capable of forcing the napkin into an arcuate shape, thereby improving its fit.

It is still another object of the invention that the apparatus be adapted to facilitate the formation of pseudo-wings to protect the under garment from soiling.

It is yet another object of the invention that the apparatus be capable of being adapted to facilitate the proper positioning of wings in a winged napkin.

These and other objects are accomplished in an absorbent article for use in conjunction with an undergarment in the perineal area of the body having front and rear transverse edges defining the length of the absorbent article, approximately longitudinally extending first and second edges, a garment facing side, and a semi-rigid elastic frame for distributing at least a portion of the forces imposed on the article by the body over a major portion of the article and for transmitting at least a portion of the forces imposed on the article to the undergarment. The frame has (i) first and second approximately longitudinally extending members having first and second transversely outboard edges, respectively, the first and second outboard edges disposed a predetermined distance transversely inboard from the first and second longitudinally extending edges, respectively, (ii) first and second tabs extending inwardly for floatingly and pivotally attaching the absorbent article to the crotch of a panty, each of the tabs having a base portion and a tip portion, the base portions attached to the garment facing side, the tip portions extending from the base portions, and (iii) first and second transversely extending members for increasing the transverse compression resistance of the absorbent article, the transversely extending members connecting the first and second approximately longitudinally extending members, the first transversely extending member attached to the garment facing side a predetermined distance from the front transverse edge, the predetermined distance being within the front 40% of the absorbent article length.

DESCRIPTION OF THE PREFERRED EMBODIMENT

Figure 1:
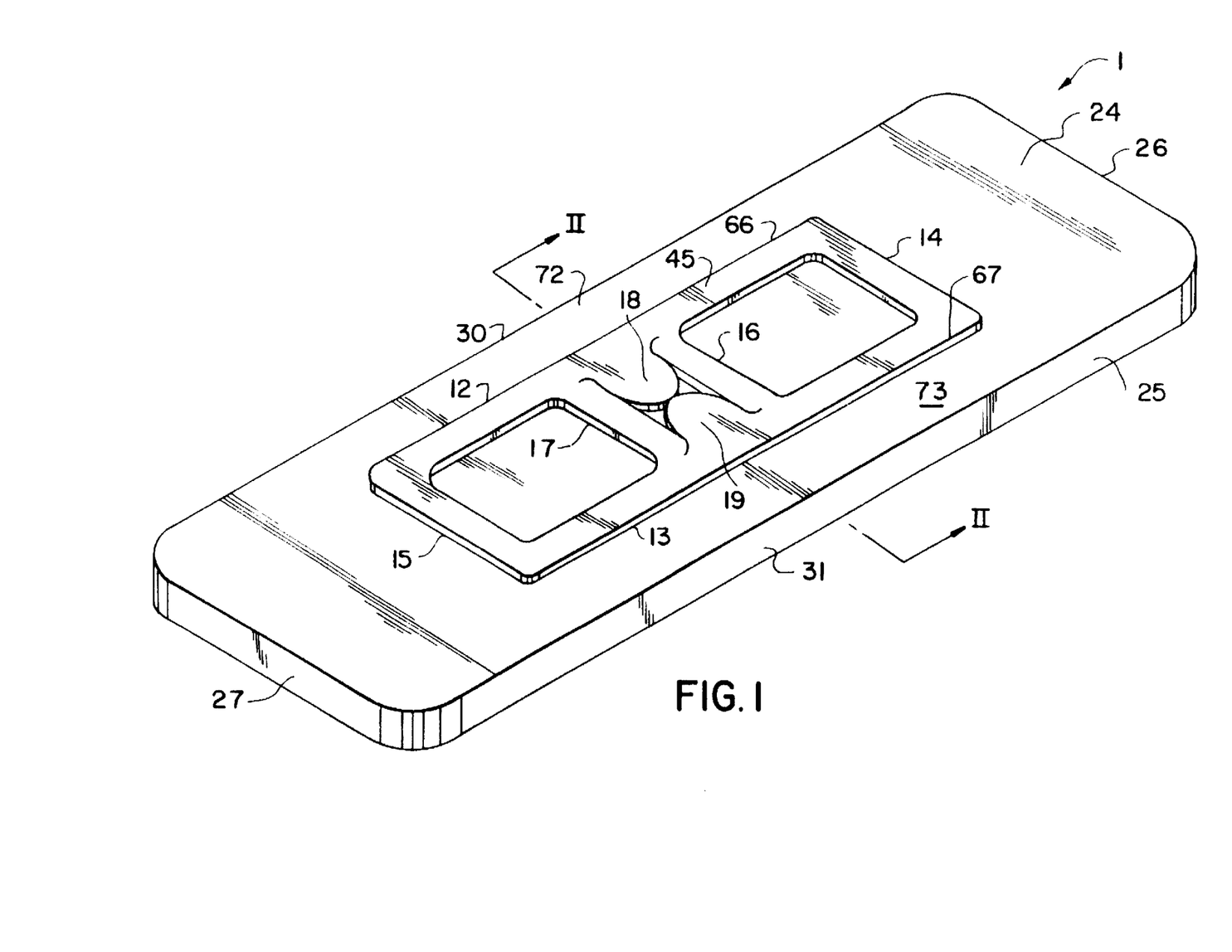
FIG. 1 is an isometric view of a sanitary napkin according to the current invention.

There is shown in FIG. 1 a sanitary napkin 1 according to the current invention. The napkin 1 is comprised of a body portion 25 and a frame 45. The body portion 25 has two longitudinally extending edges 30, 31 which define the width of the napkin and front and rear transversely extending edges 26 and 27, respectively, which define the length of the napkin.

Figure 4:
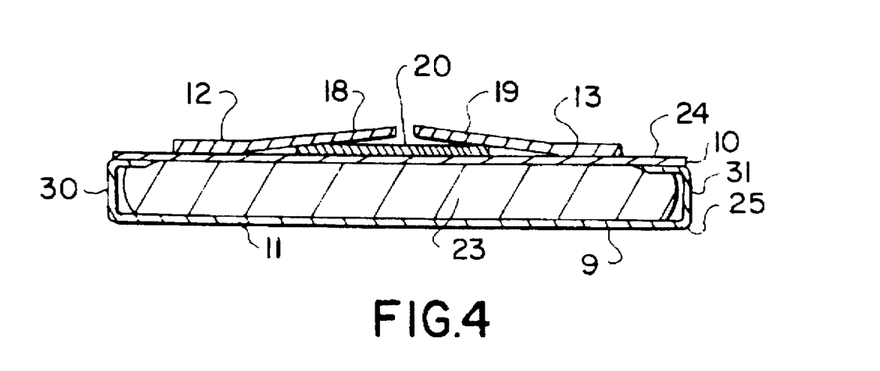
FIG. 4 is a cross-section through line IV—IV shown in FIG. 3.

As shown in FIG. 4, the body portion 25 is also comprised of an absorbent core 23. As is known in the art, the absorbent 23 core may be comprised of a tightly associated absorbent hydrophilic material such as cellulose fibers, wood pulp, regenerated cellulose or cotton fibers, or other absorbent materials generally known in the art, including peat moss, super-absorbent materials, meltblown polyolefins, synthetic wood pulp, polyolefin powders, and hydrophobic staple fiber, e.g. polyesters, nylon. Also, the absorbent core can include premade absorbent composites.

The side 9 of the napkin, which is intended to be worn against the body of the user, is covered by a body-fluid pervious cover 11 which at least partially encloses the absorbent core 23. The cover 11 can be any relatively non-absorbing fluid pervious material. This material is provided for comfort and directs fluid to an underlying layer, for example, wood pulp, which retains the fluid. The cover should retain little or no fluid in its structure to provide a relatively dry surface next to the skin. The fluid pervious cover 11 is preferably a non-woven fabric made of fibers or filaments of thermoplastic polymers such as polyethylene or polypropylene, or an apertured polymeric film.

Generally, the fluid pervious cover 11 is a single, rectangular sheet of material having a width sufficient to cover the body facing side 9 of the napkin. As shown in FIG. 4, the fluid pervious cover 11 may extend around the edges 30, 31 in a C-shaped configuration. Preferably, the fluid pervious cover 11 is longer than the core 23 so as to form end tabs, which may be sealed to the impervious barrier 10, discussed below, to fully enclose the core.

The body portion 25 of the napkin 1 further comprises a body fluid impervious barrier 10 on its garment facing side 24, which also at least partially encloses the absorbent core 23. The impervious barrier 10 may be heat sealed or attached to the pervious cover 11 by an adhesive. The impervious barrier 10 may comprise any thin, flexible, body fluid impermeable material such as a polymeric film—for example, polyethylene, polypropylene, cellophane—or even a normally fluid pervious material that has been treated to be impervious, such as impregnated fluid repellent paper or non-woven fabric material.

Alternatively, the body portion 25 of the napkin could be formed from an absorbent core having integral body facing 9 and garment facing 24 sides—that is, without separate layers of a body fluid pervious cover 9 and a body fluid impervious barrier 10.

The frame 45 is attached to the garment facing side 24 of the napkin body 25 by any suitable adhesive, preferably a hot melt adhesive, or by thermal welding. As shown in FIG. 1, the frame 45 is comprised of two longitudinally extending members 12 and 13 which are connected at their distal ends by front and rear transversely extending members 14 and 15, respectively. Two opposing tabs 18, 19 extend transversely inward from the center of each longitudinally extending member 12, 13 so that the longitudinally extending members form the base of each tab. Unlike the remainder of the frame 45, the tabs, except for the aforementioned bases, are not attached to the garment facing side 24. Additionally, transversely extending members 16, 17 connect the portions of the longitudinally extending members 12, 13 which form the bases of the tabs 18, 19.

As discussed further below, the frame 45 must be formed from material having a low modulus of elasticity and a large elastic range, such as would be provided by plastics with a room temperature flexural modulus in the range of $250 \times 10^3$ psi to $1200 \times 10^3$ psi, so that the frame can respond to the application of modest force from the user's body by resisting deformation without fracture. Accordingly, in the preferred embodiment, the frame 45 is injection molded from a polymer. Alternatively, the frame may be die cut from a sheet of plastic polymer.

Figure 3:
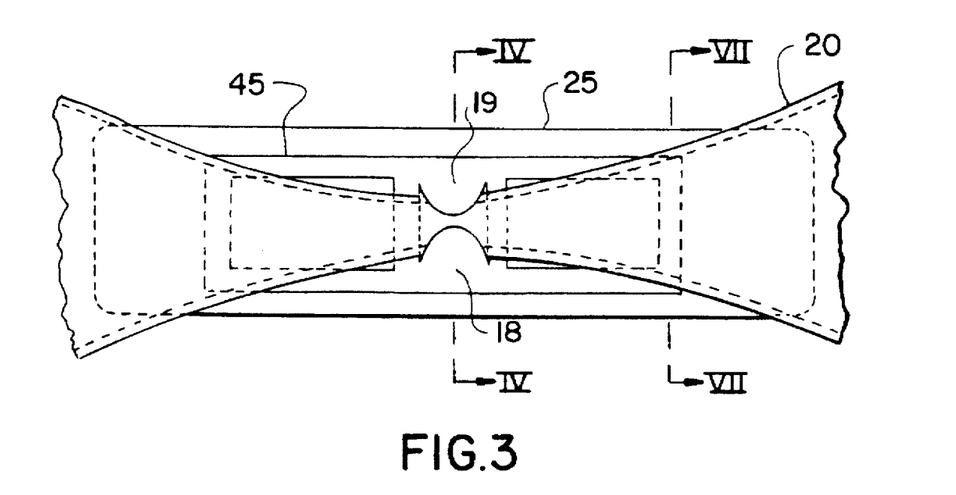
FIG. 3 is a plan view, from below, of the napkin shown in FIG. 1 as attached to the crotch of a panty.

The frame 45 aids the napkin in resisting permanent deformation from the forces imposed on it by the user's body in three ways. First, as shown in FIG. 3, the frame serves as a device for floatingly attaching the napkin to a panty crotch so that the napkin can respond to the forces by moving relative to the panty crotch. This floating action includes the ability of the napkin to slide over the panty crotch as well as pivot relative to the panty about the tabs 18, 19. Thus, at least with respect to small forces imposed by the user's legs, the napkin need not deform at all, but can move away from the user's legs as though it were a rigid body so as not to interfere with the user's motion.

The relative motion between the napkin and the panty provided by the current invention can be contrasted to prior art devices held in fixed relation to the panty by adhesive, wherein even minor interference between the napkin and the user's body was resisted by the panty elastic and resulted in either (i) local deformation of the napkin, if it was of the type without reinforcing means or (ii) an awareness, and the attendant discomfort, by the user of a resisting pressure, if the napkin was of the reinforced type, such as disclosed in U.S. Pat. No. 4,865,597 (Mason et al.). According to the current invention, this relative motion not only prevents forces applied by the thighs directly to the napkin from deforming the napkin, it also prevents small forces from indirectly acting on the napkin through the strain in the panty elastic. As a result, the napkin is less likely to deform and is more comfortable. The floating and pivoting action necessary to allow such relative motion is facilitated by the transversely and longitudinally extending member 12–17, discussed below, which give the napkin sufficient rigidity to move as a rigid body, rather than merely locally deforming under the action of a locally applied force.

Second, to the extent that the rigid body motion discussed above is not sufficient to ameliorate the force imposed on the napkin—that is, if the interference between the user's body and the napkin exceeds its ability to float on the panty—the frame serves to transmit the forces imposed on the napkin to the elastic in the panty crotch. The panty elastic can undergo sufficient extension to absorb a moderate force without generating a reaction force large enough to deform the napkin.

Third, to the extent that neither the rigid body motion nor the panty elastic extension discussed above is sufficient to completely ameliorate the force imposed on the napkin, the frame serves to distribute the remaining force over a large portion, preferably a major portion, of the napkin, rather than having it concentrated at the point of contact with the user's body as occurred in prior art napkins. As a result, although the napkin deforms, the local strain on the napkin, and, therefore, the potential for permanent deformation, is minimized.

As discussed further below, in addition to providing deformation resistance, the frame allows the napkin to be shaped in novel ways.

Figure 2:
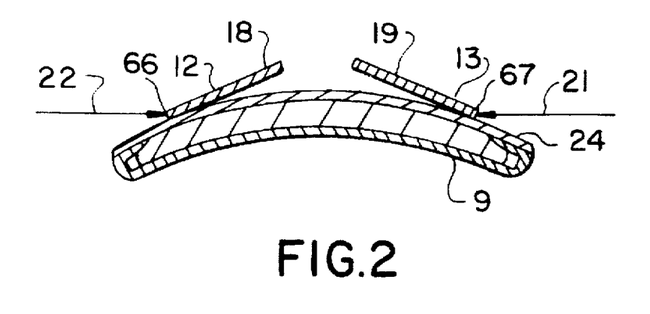
FIG. 2 is a cross-section through line II—II shown in FIG. 1 when compressive forces are applied to the frame in preparation for attaching the sanitary napkin to an undergarment.

The attachment function is provided by the tabs 18, 19. As shown in FIGS. 3 and 4, the napkin 1 is applied to the crotch of a panty 20 by placing the center portion of the crotch underneath the tabs 18, 19—that is, between the tabs and the transversely extending members 16, 17. This operation is facilitated by applying compressive forces 21, 22 to the outboard edges 66, 67 of the portions of the longitudinally extending members 12, 13 which form the bases of the tabs so that the frame is bent outward, thereby causing the tabs to open, as shown in FIG. 2.

Figure 5:
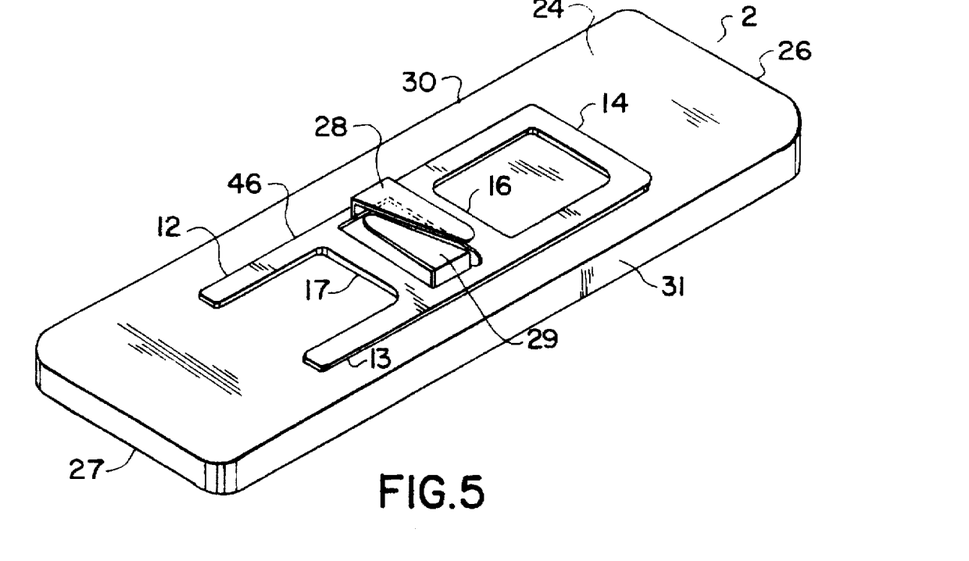
FIGS. 5 and 6 are isometric views of alternative embodiments of the napkin shown in FIG. 1.

The tabs 18, 19 shown in FIG. 1 lay in the plane of the frame 45. The ability of the napkin to float by sliding on the panty crotch can be increased by forming the tabs 28, 29, shown in FIG. 5, so that they extend in a plane spaced above and parallel to the plane of the frame 46, thereby ensuring that adequate clearance exists to permit relative motion between the panty elastic and the tabs. Note that the tabs 28, 29 shown in FIG. 5 are longitudinally asymmetric. This arrangement allows longer tabs to be die cut from the plastic sheet than is possible with the symmetric tabs shown in FIG. 1.

The force transmitting and distributing functions of the frame 45 are provided by the longitudinally 12, 13 and transversely 14–17 extending members. In order for these members to properly transmit and distribute the forces imposed on the napkin, they have a minimum of flexural rigidity. However, notwithstanding the aforementioned floating and pivoting action, if the transverse force imposed on the napkin by the legs of the user is sufficiently great, the force will ultimately be elastically resisted by the transversely extending members 14–17. Thus, the frame must be an essentially elastic semi-rigid member—that is, sufficiently flexible to buckle and bend under modest compressive forces so that the user is not aware of pressure from the frame, yet sufficiently rigid to distribute the force throughout the napkin and transmit it to the more compliant undergarment. In this way, the napkin is prevented from permanently deforming or roping during use.

Figure 16:
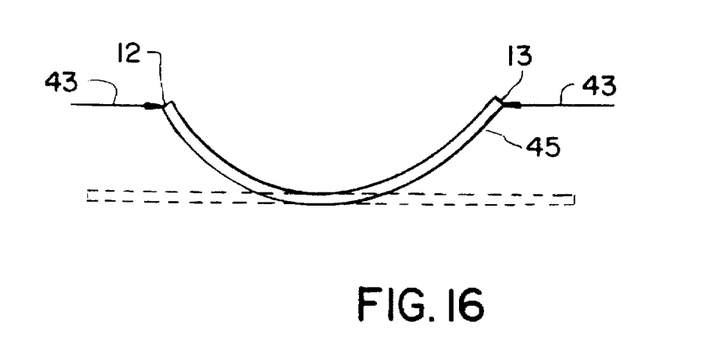
FIG. 16 shows the transverse member undergoing compressive bending.

Referring to FIG. 16, the compressive bending resistance of the frame 45 is defined as the compressive force 43 required to reduce by 60% the projected width of the frame—that is, so that dimension B is 60% of dimension C—when applied to the edges 66, 67 of the frame at a rate of 5 inches per minute. In the preferred embodiment, the compressive bending resistance of the frame is in the range of approximately 0.3 to 5.5 pounds. This is achieved by forming one or more of the members 14–17 from plastic sheet having a room temperature flexural modulus in the range of $250 \times 10^3$ to $1200 \times 10^3$ psi, preferably $275 \times 10^3$ to $400 \times 10^3$ psi, and a thickness in the range of approximately 0.005 to 0.040 inch and having a width in the transverse direction of approximately ¼ inch. If the individual members are all of the same width, the compressive bending resistance of each member is approximately the compressive bending resistance of the frame divided by the number of members.

Since it is anticipated that the frame 45 will be subjected to considerable compressive bending, the material from which it is formed should have sufficient elasticity to allow the frame to be bent so that the longitudinally extending outboard edges 66, 67 come together without yielding of the material forming the transverse members 14–17. Such elasticity will allow the frame to recover its original shape when subjected to such compressive bending. Accordingly, in the preferred embodiment, the material from which the frame is formed has a 0.2% offset yield strength in the range of 2000 to 8000 psi.

In the preferred embodiment, the frame is formed from a polymer such as a random copolymer of polypropylene with polyethylene, recycled polyethylene terephelate, polyvinyl alcohol (water soluble), an acrylic polymer (especially of the water dispersable type), polycarbonate or cellulose acetate. A preferred material for the frame is a polypropylene random copolymer, such as Eastman P5M2Z-012, in a thickness of approximately 0.010 inch.

It is important to have at least one transversely extending member at the approximate center of the napkin. Additional transversely extending members may be arranged in various fashions along the length of the napkin. As shown in FIG. 1, the transversely extending members 14–17 are spaced along the length of the frame—members 14 and 15 being at the distal ends and members 16 and 17 being in the center portion of the longitudinally extending members 12, 13. In order to provide geometric stability in both the front and rear of the napkin 1, the transverse member 14, 15 are disposed in the forward and rear portions of the napkin.

Accordingly, in the preferred embodiment, the front 14 and rear 15 transversely extending members are spaced apart approximately 2 to 5 inches. When the frame 45 is applied to typical length napkins (i.e., approximately 9 inches long), front member 14 is disposed within the front 40% of the napkin length, preferably the centerline of the member 14 is disposed a distance back from the front edge 26 of the napkin in the range of approximately 20% to 40% of the napkin length L. Rear member 15 is disposed within the rear 40% of the napkin length, preferably the centerline of the member 15 is disposed a distance Y back from the front edge of the napkin in the range of approximately 60% to 80% of the napkin length L. Alternatively, for certain products—such as, products which are intended to be worn tightly against the body, due either to their design or the characteristics of the undergarment, products which are intended for overnight use or for use in a reclining position, and for longer products—it may be desirable to eliminate the rear transversely extending member 15, as shown in FIG. 5, so as to allow the rear of the napkin 2 to advantageously compress and enter between the buttocks. The tabs 18, 19 and the transversely extending members 16, 17 are most advantageously disposed in approximately the mid-point of the frame 45—that is, in an area approximately 40% to 60% of the napkin length L back from the front edge 26.

Those skilled in the art will appreciate that when the frame is applied to atypical length napkins, such as napkins having a length in excess of 10 inches, or napkins intended to be worn asymmetrically within the perineal area, such as napkins having extended rear portions, the aforementioned percentage dimensions should be revised in light of the teaching contained herein—specifically, the transversely extending members should be spaced so as to provide adequate deformation resistance within the portion of the napkin disposed in the perineal area.

Figure 14:
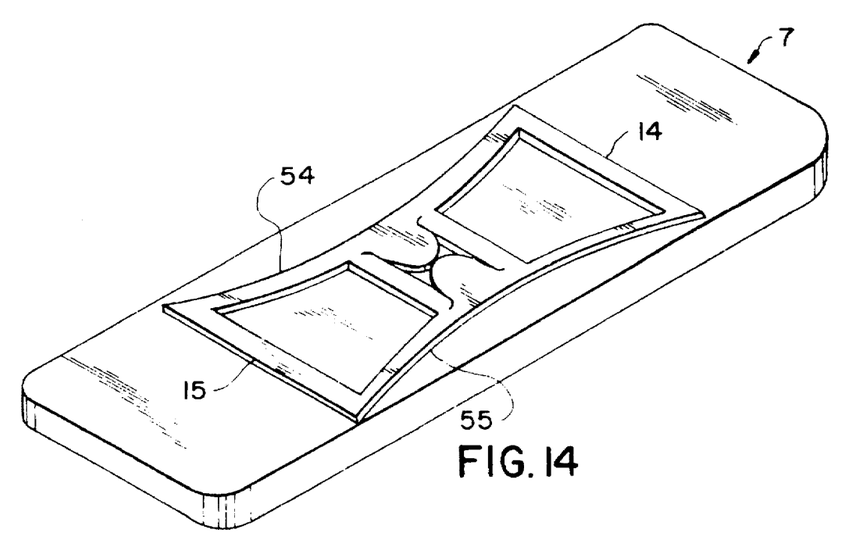

In the preferred embodiment, the distance between the outboard edges 66, 67 of the longitudinally extending members is less than 3 inches, preferably in the range of approximately 1 to 2 inches and at least one-half inch less than the width of the napkin. The length of the longitudinally extending members is approximately 3 to 5 inches, thereby allowing the frame to distribute the forces imposed on the napkin over a relatively large portion, preferably a major portion, of the napkin. As a result, the length to width ratio of the frame is greater than 1:1. Note that the distance between the outboard edges 66, 67 of the longitudinally extending members 12, 13 defines the length of the transversely extending members 14–17. The longitudinally extending members 12, 13 also serve to distribute the deformation resisting force generated by the transversely extending members 14–17 along a large portion of the user's leg, so that the user is not aware of these crush resisting forces. To this end, the longitudinally extending members 54, 55 can be formed into a arcuate shape in the plane of the garment facing side 24 in order to conform to the shape of the leg, as shown in FIG. 14.

Figure 6:
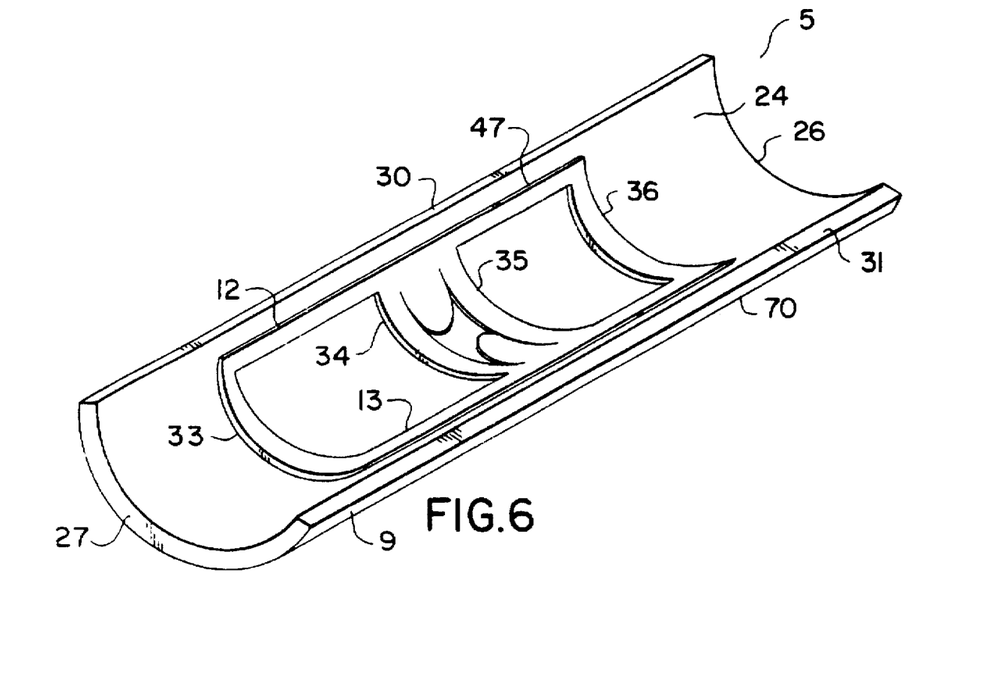
Figure 7:
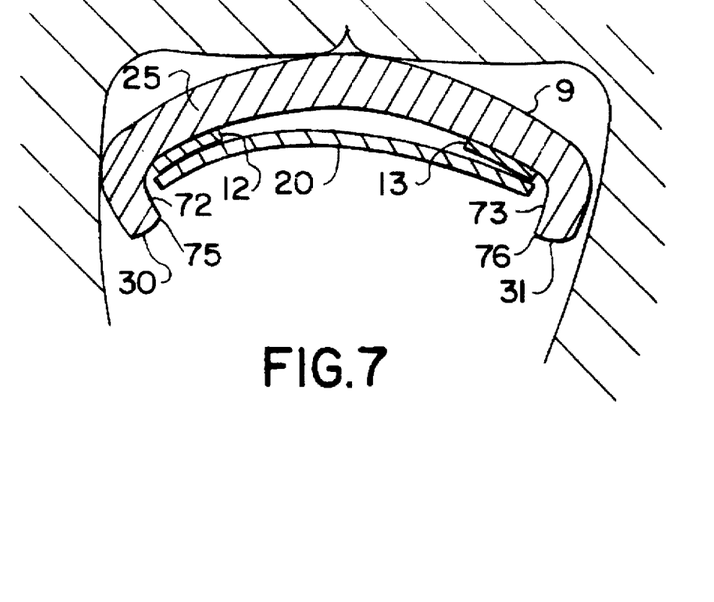
FIG. 7 is a cross-section through line VII—VII shown in FIG. 3 showing the napkin in use.

A further advantage of the semi-rigid nature of the frame is that by pre-forming the frame into an arcuate shape, the frame will force the body portion 25 of the napkin 5 to assume a similar shape. Thus, as shown in FIG. 6, the transversely extending members 33–36 of the frame 47 can be pre-formed, —for example, by hot setting—so as to have an arcuate shape in the transverse direction. Such a frame would, when attached to the garment facing side 24, force the napkin body portion 70 into a transversely arcuate shape so that the garment facing side 24 forms a transversely concave surface and the body facing side 9 forms a transversely convex surface, as shown in FIG. 6. The inventor has discovered that such shaping would improve the fit, and therefore, the performance of the napkin since it would ensure that the napkin contacted the user's body along the longitudinal centerline of the napkin, as shown in FIG. 7. Such contact avoids having fluids run along the surface of the body and contacting the napkin in a less than desirable location from the standpoint of absorbency. The arcuate shape also makes the napkin more comfortable to wear because the frame 47 is more easily bent by transverse compressive forces so that the user is less aware of the crush resistance provided by the frame.

Figure 13:
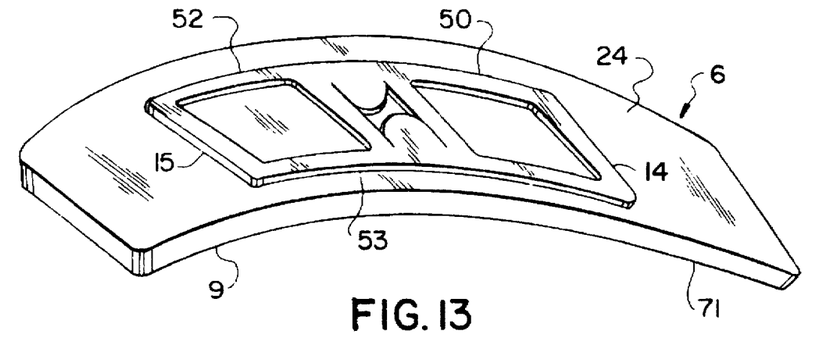
FIG. 13–15 are alternate embodiments of the napkin shown in FIG. 1.

As shown in FIG. 13, the longitudinally extending members 52, 53 of the frame 50 could also be preformed into a longitudinally arcuate shape, thereby forcing the napkin body portion 71 into a similar shape. Such shaping would facilitate the longitudinal fit of the napkin 6.

Figure 17:
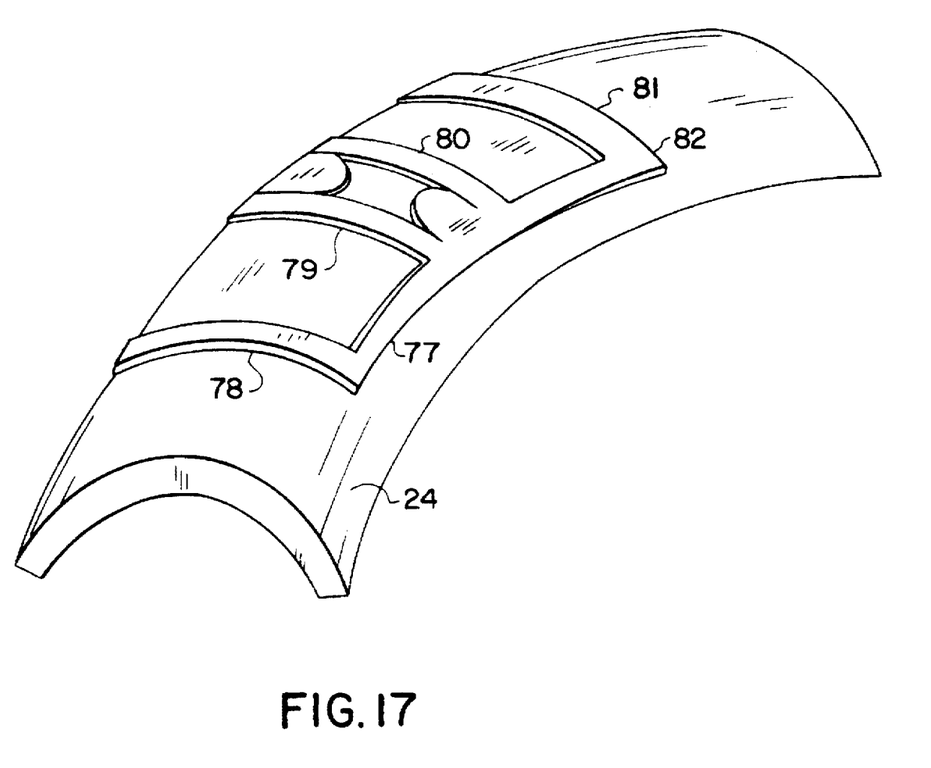
FIG. 17 is an isometric view of an alterante embodiment of the napkin shown in FIG. 1.

As shown in FIG. 17, both the longitudinally extending members (only one, member 77, of which is visible in FIG. 17) and the transversely extending members 78–81 can be preformed into an arcuate shape so that the napkin is formed into an arcuate shape in both the longitudinal and transverse directions. Thus, as shown in FIG. 17, the frame 82 can be preformed so that the garment facing side 24 is convexly curved, as well as the body facing side being concavely curved, in both the longitudinal and transverse directions.

As shown in FIG. 1, according to another important aspect of the invention, the transversely outboard edges 66, 67 of the longitudinally extending members 12, 13 are spaced a distance A inward from the longitudinally extending edges 30, 31 of the napkin body portion 25. As a result, portions 72, 73 of the napkin body overhang the frame 45. This arrangement allows the overhanging portions 72, 73 to conform to the user's legs, thereby providing a seal comparable to that obtained by incorporating wings or tabs onto the longitudinally extending sides of the napkin. Moreover, since the frame is attached to the garment facing side, if the overhanging portions 72, 73 are sufficiently wide, the user's legs will bend them downward around the longitudinally extending members 12, 13 and, therefore, around the panty crotch 20, as shown in FIG. 7. Thus, the overhanging portions 72, 73 form pseudo-wings 75, 76 which protect the panty crotch from soiling and which provide further geometric stability of the napkin. In the preferred embodiment, the distance A is at least ¼ inch, preferably approximately ½ inch. It should be noted that forming a transversely arcuate frame 47, such as that shown in FIG. 6, will facilitate the downward bending of the overhanging portions 72, 73 and, therefore, the formation of the pseudo-wings 75, 76.

Figure 8:
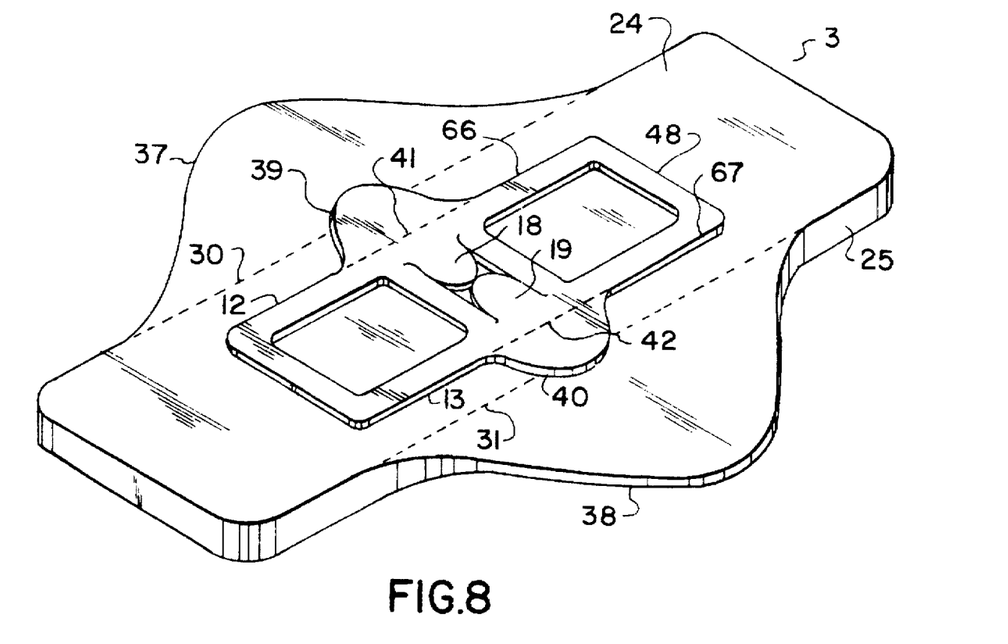
FIG. 8 is a alternate embodiment of the invention as applied to a winged napkin.
Figure 9:
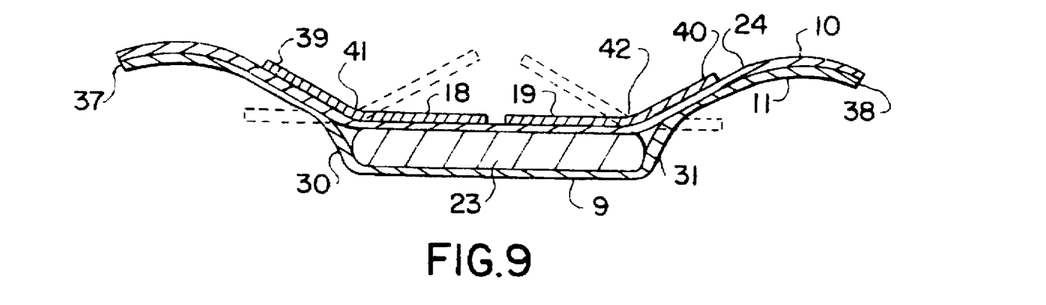
FIG. 9 is a transverse cross-section through the center portion of the napkin shown in FIG. 8 after the outward extending tabs have been pre-bent.

According to another embodiment of the invention, shown in FIG. 8, the napkin body portion 25 may be formed so that wings 37, 38 extend transversely from the longitudinally extending edges 30, 31, respectively. As shown in FIG. 9, such wings 37, 38 may be formed by extending the body fluid pervious cover 9 and the body fluid impervious barrier 10 beyond the absorbent core 23 and attaching them together. Alternatively, the wings may be separately formed from other materials and attached to the napkin body 25 and may also contain additional absorbent layers. As shown in FIGS. 8 and 9, in such a winged napkin 3, tabs 39, 40 extend transversely outwardly from the longitudinally extending members 12, 13 of the frame 48, respectively, opposite the inwardly extending tabs 18, 19. Hinges 41, 42 are formed in the tabs 39, 40 in line with the outboard edges 66, 67 of the longitudinally extending members 12, 13 so that the tabs preferentially bend at the hinge locations. The hinges 41, 42 may be created by forming weakened areas in the tabs 39, 40—for example, by crimping.

Figure 10:
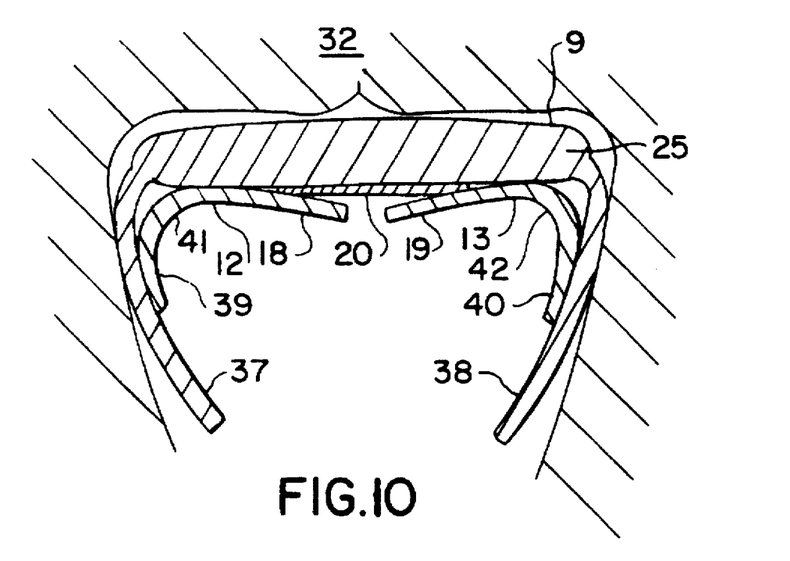
FIG. 10 is a transverse cross-section through the center portion of the napkin shown in FIG. 8 in use.

As shown in FIG. 10, when the napkin is in use, the user's legs bend the tabs 39, 40 inward and downward about hinges 41, 42 so that the tabs press the wings 37, 38 against the user's legs, thereby forming a gasket which prevents fluid from escaping from the perineal area. In the preferred embodiment, the wings 37, 38 are attached to the tabs 39, 40 with adhesive to ensure that the wings are properly extended around the tabs. As depicted in FIG. 8, the tabs 39, 40 lie in the plane of the frame 66. However, the tabs may be pre-bent about hinges 41, 42 so as to form an oblique angle with the plane of the frame, as shown in FIG. 9. Pre-bending facilitates the bending of the tabs 39, 40 and also provides a lever which may be advantageously used to bend the inwardly extending tabs 18, 19 into an open position, as shown in phantom in FIG. 9, to allow insertion of the panty crotch.

Figure 11:
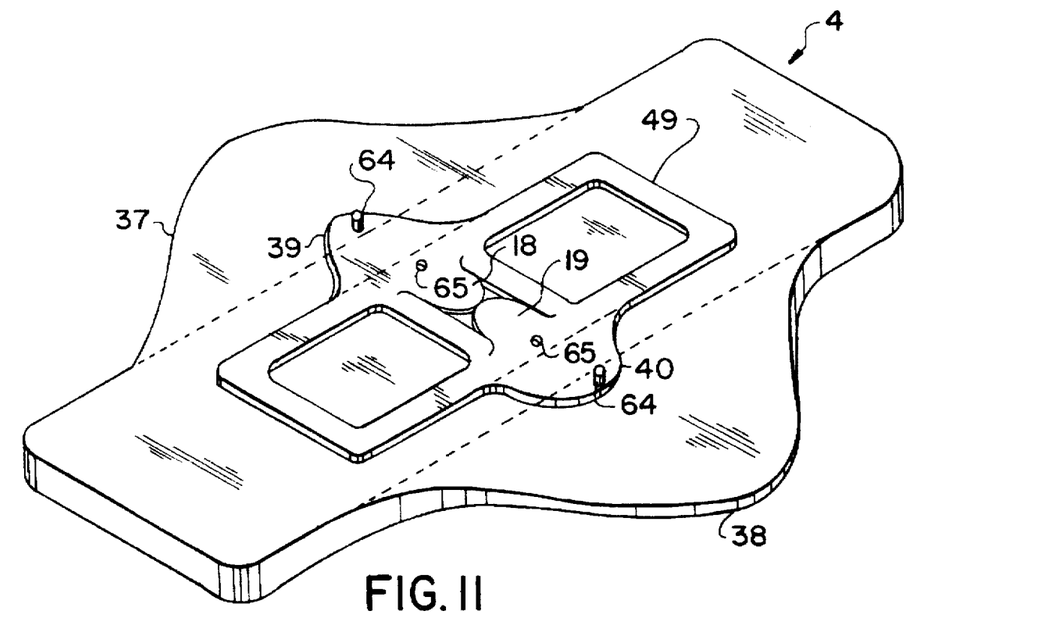
FIG. 11 is an alternate embodiment of the napkin shown in FIG. 8.
Figure 12:
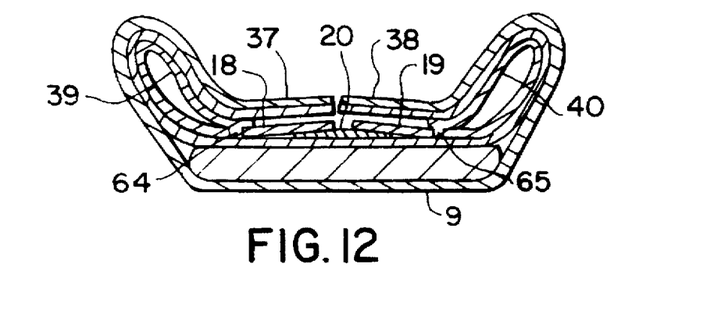
FIG. 12 is a transverse cross-section through the center portion of the napkin shown in FIG. 11 after the outward extending tabs have been bent over themselves and the posts secured in the holes.

According to another embodiment of the invention, posts 64 may be formed on each outwardly extending tab 39, 40 which are adapted to engage holes 65 in the longitudinally extending member 12, 13 of the frame 49, as shown in FIG. 11. The diameter of the holes 65 is smaller than that of the posts 64 so that, once inserted, the posts are retained in the holes by a compression fit. As shown in FIG. 12, after the panty crotch 20 has been inserted under the inwardly extending tabs 18, 19, the posts 64 are inserted and secured into the holes 65 by bending the outwardly extending tabs 39, 40 back upon themselves. Since the wings 37, 39 are attached to outwardly extending tabs 39, 40, this bending action ensures that the wings are wrapped around the panty crotch 20, thereby preventing it from being soiled. In addition, the rounded edges formed by the bent tabs 39, 40 provide a smooth and comfortable surface for application of the crush resisting forces of the frame 49 against the user's legs.

Figure 15:
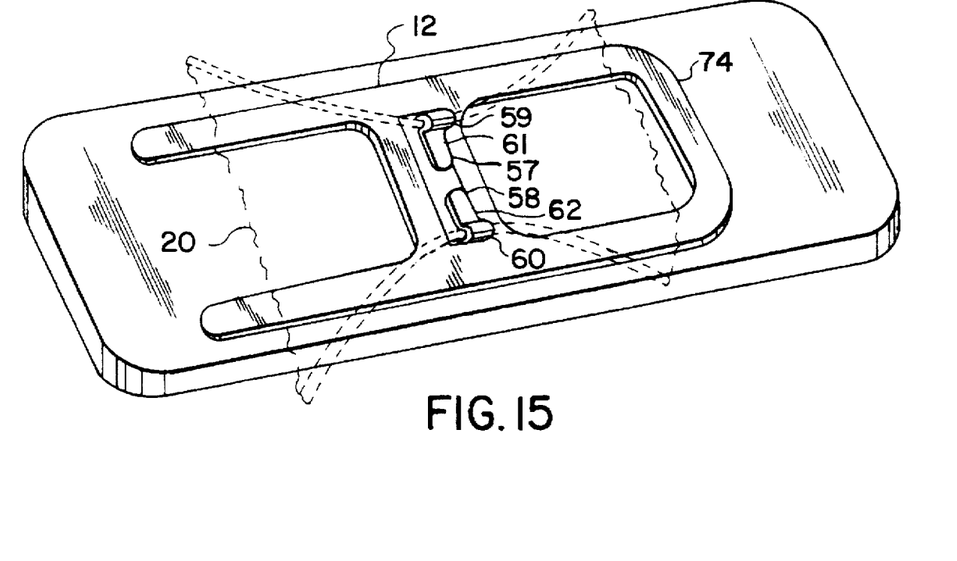

It will be appreciated that, in some cases, insertion of the panty crotch underneath the tabs 18, 19 will result in the crotch being excessively bunched in the center portion of the frame, causing discomfort. This bunching can be avoided by the tab configuration shown in FIG. 15, in which each tab 57, 58 is comprised of (i) a first portion 59, 60 having an approximately inverted U-shape extending by the first leg of the "U" from the inboard edge of the longitudinally extending members 12, 13 in a direction away from the plane of the garment facing side 24, and (ii) a second planar portion 61, 62 extending inwardly from the second leg of the "U" in a direction substantially parallel to the plane of the garment facing side. As shown in FIG. 15, the cavities created by the "U"-shaped portions 59, 60 trap the elastic bands 63 on the edges of the panty crotch leg openings, thereby ensuring that the crotch extends across the full distance between the tabs 57, 58 and is not bunched in the center of the frame 74. The planar portions reduce the likelihood that the panty crotch will slip out from under the tabs.

Although the invention has been described with reference to a sanitary napkin, it should be appreciated that the invention is equally applicable to other types of absorbent articles intended for use in the perineal area of the body, such as panty shields, incontinence pads, nursing pads, diapers and the like. Moreover, the present invention may be embodied in other specific forms without departing from the spirit or central attributes thereof and, accordingly, reference should be made to the appended claims, rather than to the foregoing specification, as indicating the scope of the invention.

What is claimed:

1. An absorbent article comprising:
   a) front and rear transverse edges defining an absorbent article length of said absorbent article therebetween;
   b) a garment facing side;
   c) first and second tabs for attaching said absorbent article to a panty crotch, each of said tabs having a base portion and a tip portion, said base portions attached to said garment facing side, said tip portions extending from said base portions; and
   d) a semi-rigid elastic frame comprising:
      i) a first transversely extending member for providing resilient resistance to permanent transverse deformation of said absorbent article, said first transversely extending member attached to said garment facing side a predetermined distance from said front transverse edge, said predetermined distance being within 40% of said absorbent article length; and
      ii) a second transversely extending member for providing further resilient resistance to permanent transverse deformation of said absorbent article, said second transversely extending member attached to said garment facing side a predetermined distance from said rear transverse edge, said predetermined distance being within 40% of said absorbent article length;

wherein said first and second transversely extending members have a flexural modulus in the range of $250 \times 10^3$ to $1200 \times 10^3$ psi at room temperature.

2. The absorbent article according to claim 1 wherein said first and second tabs are disposed in a longitudinally asymmetric arrangement.

3. The absorbent article of claim 1 wherein the semi-rigid elastic frame is floatingly attached to the garment facing side.

4. The absorbent article according to claim 1 further comprising first and second longitudinally extending members forming said base portions of said first and second tabs, respectively.

5. The absorbent article according to claim 4 wherein said absorbent article has first and second longitudinally extending edges, said first and second longitudinally extending members being disposed at least ¼ inch inboard from said first and second longitudinally extending edges, respectively.

6. The absorbent article according to claim 4 wherein said first transversely extending member connects said first and second longitudinally extending members.

7. The absorbent article according to claim 6 wherein said second transversely extending member connects said first and second longitudinally extending members, said second transversely extending member attached to said garment facing side a predetermined distance from said front transverse edge, said predetermined distance being between 60% and 80% of said absorbent article length.

8. The absorbent article according to claim 7 further comprising a body facing side, and wherein said first and second transversely extending members form said article into a transversely arcuate shape, said garment facing side having a transversely concave surface and said body facing side having a transversely convex surface.

9. An absorbent article having first and second longitudinally extending edges, comprising:

a) a garment facing side opposite a body facing side; and
b) a semi-rigid elastic frame attached to said garment facing side, said frame having first and second longitudinally extending members and a first transversely extending member having a flexural modulus in the range of 250×10³ to 1200×10³ psi at room temperature for providing resilient resistance to permanent transverse deformation of said absorbent article and connecting said longitudinally extending members, said first and second longitudinally extending members having first and second transversely outboard edges, respectively, said first and second outboard edges disposed about one-quarter inch transversely inboard from said first and second longitudinally extending edges, respectively.

10. The absorbent article according to claim 9 further comprising a second transversely extending member connecting said longitudinally extending members, and wherein said first and second transversely extending members form said garment facing side into a transversely concave surface and said body facing side into transversely convex surface.

11. The absorbent article according to claim 9 wherein said frame is formed from a polymer.

12. The absorbent article according to claim 11 wherein said polymer is selected from the group consisting of: a random copolymer of polypropylene with polyethylene, recycled polyethylene terephalate, polyvinyl alcohol and acrylic polymer.

13. An absorbent article having first and second longitudinally extending edges, comprising:

a) a garment facing side opposite a body facing side;
b) a semi-rigid elastic frame attached to said garment facing side, said frame having first and second longitudinally extending members and first and second transversely extending members having a flexural modulus in the range of 250×10³ to 1200×10³ psi at room temperature for providing resilient resistance to permanent transverse deformation of said absorbent article and connecting said longitudinally extending members, said first and second longitudinally extending members positioned laterally inward from the longitudinal edges of said absorbent article, and said first and second transversely extending members preforming said garment facing side into a concave surface and said body facing side into convex shape.

14. An absorbent article having first and second longitudinally extending edges comprising:

a) a garment facing side;
b) first and second wings extending transversely from said first and second longitudinally extending edges, respectively, and
c) a semi-rigid elastic frame attached to said garment facing side, said frame having (i) first and second longitudinally extending members which are disposed laterally inward from the longitudinally extending edges of said absorbent article, (ii) a first transversely extending member for providing resilient resistance to permanent transverse deformation of said absorbent article and connecting said longitudinally extending members, and (iii) first and second outwardly extending tabs extending from said first and second longitudinally extending members, respectively in the region of said first and second wings.

15. The absorbent article according to claim 14 wherein said frame further comprises a hinge formed between each of said first and second outwardly extending tabs and each of said first and second longitudinally extending members.

16. The absorbent article according to claim 14 wherein said outwardly extending tabs extend at an oblique angle to a plane defined by said frame.

17. The absorbent article according to claim 14 wherein said outwardly extending tabs are configured to bend elastically inward when force is applied to said outwardly extending tabs, thereby generating a resisting force pressing against said wings.

18. The absorbent article according to claim 14 wherein said outwardly extending tabs are configured to be elastically bent inward by a wearer when said absorbent article is installed into a perineal area of the wearer.

19. The absorbent article according to claim 14 further comprising detachable means for attaching said first and second outwardly extending tabs to said first and second longitudinally extending members, respectively.

20. The absorbent article according to claim 19 wherein said first and second outwardly extending tabs are attached to said first and second wings, respectively.

21. The absorbent article according to claim 14 wherein said frame further comprises third and fourth inwardly extending tabs adapted to attach said absorbent article to a panty, said third and fourth inwardly extending tabs extending from said first and second longitudinally extending members, respectively.

22. The absorbent article according to claim 21 wherein said third and fourth inwardly extending tabs are disposed adjacent and transversely opposite to said first and second outwardly extending tabs.

23. An absorbent article having a garment facing side, two longitudinal edges and two transverse edges, comprising a semi-rigid elastic apparatus attached to said garment facing side for resisting crushing of said absorbent article and which is capable of attaching said absorbent article to a panty having an elastic band along edges of a crotch portion thereof, said semi-rigid elastic apparatus comprising:

a) first and second longitudinally extending members, said longitudinally extending members being positioned laterally inward from the longitudinal edges of said absorbent article;
b) a transversely extending member for providing resilient resistance to permanent transverse deformation of said absorbent article and connecting said longitudinally extending members; and c) first and second tabs having an inverted, U-shaped portion configured to retain said elastic band, said U-shaped portion forming first and second legs, said first leg of each of said U-shaped portions extending from one of said first and second longitudinally extending members in a direction away from a plane defined by said garment facing side.

24. The apparatus according to claim 23 wherein each of said tabs further comprises a planar portion extending inwardly from said second leg of each of said U-shaped portions in a direction parallel to a plane defined by said garment facing side.

25. An absorbent article having first and second longitudinally extending edges, comprising:

a) a garment facing side;

b) a semi-rigid elastic frame attached to said garment facing side, said frame having first and second longitudinally extending members and first and second transversely extending members having a flexural modulus in the range of $250 \times 10^3$ to $1200 \times 10^3$ psi at room temperature for providing resilient resistance to permanent transverse deformation of said absorbent article and connecting said longitudinally extending members, said longitudinally extending members positioned laterally inward from the longitudinal edge of said absorbent article, said transversely extending members pre-forming said garment facing side into a convex surface and said body facing side into a concave surface in a transverse direction; and said longitudinally extending members pre-forming said garment facing side into a convex surface and said body facing side into a concave surface in a longitudinal direction.

* * * * *